United States Patent
Scheiderer et al.

(10) Patent No.: US 9,500,567 B2
(45) Date of Patent: Nov. 22, 2016

(54) SOIL SAMPLER

(71) Applicants: David Scheiderer, Milford Center, OH (US); Michel Grand, Irwin, OH (US); Dwayne Maddux, London, OH (US); Evan Delk, South Vienna, OH (US)

(72) Inventors: David Scheiderer, Milford Center, OH (US); Michel Grand, Irwin, OH (US); Dwayne Maddux, London, OH (US); Evan Delk, South Vienna, OH (US)

(73) Assignee: Integrated AG Service, LTD, Milford Center, OH (US)

( * ) Notice: Subject to any disclaimer, the term of this patent is extended or adjusted under 35 U.S.C. 154(b) by 364 days.

(21) Appl. No.: 14/285,865

(22) Filed: May 23, 2014

(65) Prior Publication Data

US 2014/0251032 A1    Sep. 11, 2014

Related U.S. Application Data

(63) Continuation-in-part of application No. 13/686,014, filed on Nov. 27, 2012, now Pat. No. 9,116,078.

(51) Int. Cl.
*G01N 1/08*    (2006.01)
*G01N 1/04*    (2006.01)
*G01N 1/02*    (2006.01)

(52) U.S. Cl.
CPC ......... *G01N 1/08* (2013.01); *G01N 1/04* (2013.01); *G01N 2001/021* (2013.01); *G01N 2001/085* (2013.01)

(58) Field of Classification Search
None
See application file for complete search history.

(56) References Cited

U.S. PATENT DOCUMENTS

| | | | |
|---|---|---|---|
| 6,044,324 A | 3/2000 | Boerhave | |
| 7,552,654 B2 | 6/2009 | Burton | |
| 8,286,857 B2 | 10/2012 | Covely | |
| 9,116,078 B1 * | 8/2015 | Scheiderer | G01N 1/04 |
| 2005/0172733 A1 * | 8/2005 | Drummond | A01B 79/005 73/864.41 |
| 2009/0071714 A1 * | 3/2009 | Shrestha | A01C 21/002 175/20 |
| 2010/0037712 A1 * | 2/2010 | Burton | E21B 7/027 73/863.11 |
| 2014/0095074 A1 | 4/2014 | Covely | |

* cited by examiner

*Primary Examiner* — Robert R Raevis
(74) *Attorney, Agent, or Firm* — Mark A. Navarre

(57) ABSTRACT

An automated soil sampler is removably mounted on an agricultural tractor and collects soil samples in a farm field while the tractor is driven through the field. At a periodic interval, the soil sampler momentarily lowers a soil collection knife into the soil to collect a soil sample, raises the collection knife out of the soil, and transfers the collected soil sample into a bar-coded storage container. The GPS location of the soil sample is associated with the storage container's bar-code in a data file. The interval between successive periodic soil samples corresponds to a determined forward displacement of the tractor. Storage containers that have received soil samples are moved to a storage area until all of the soil samples for a given field have been collected.

17 Claims, 14 Drawing Sheets

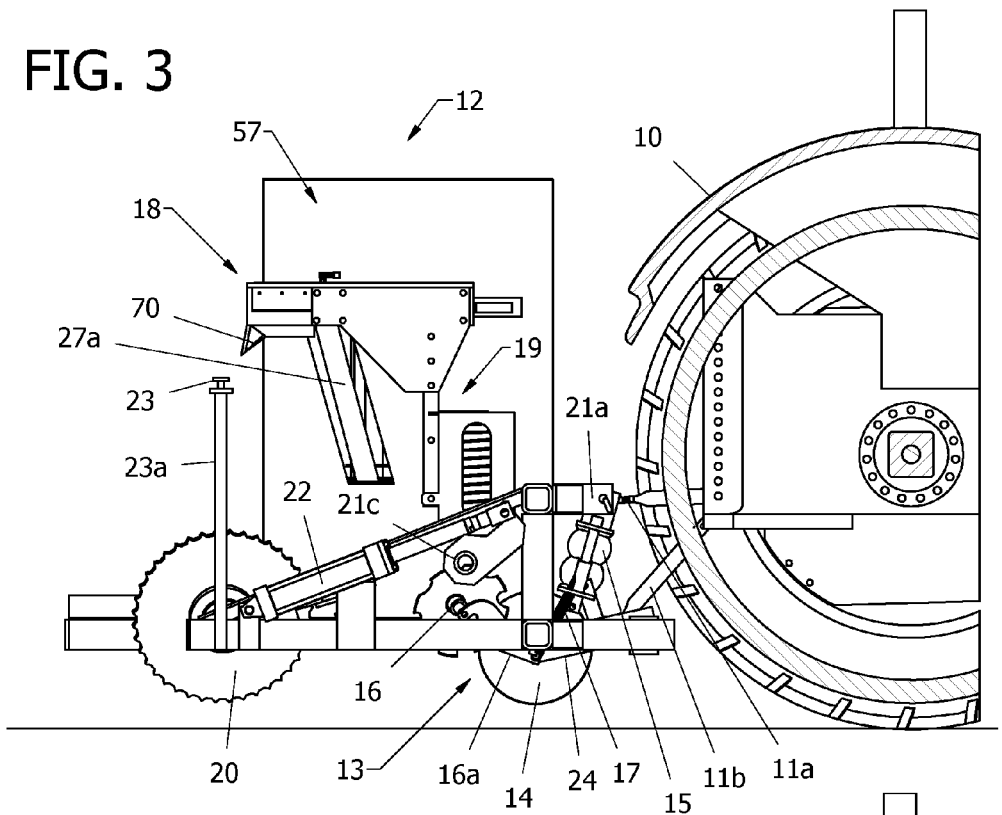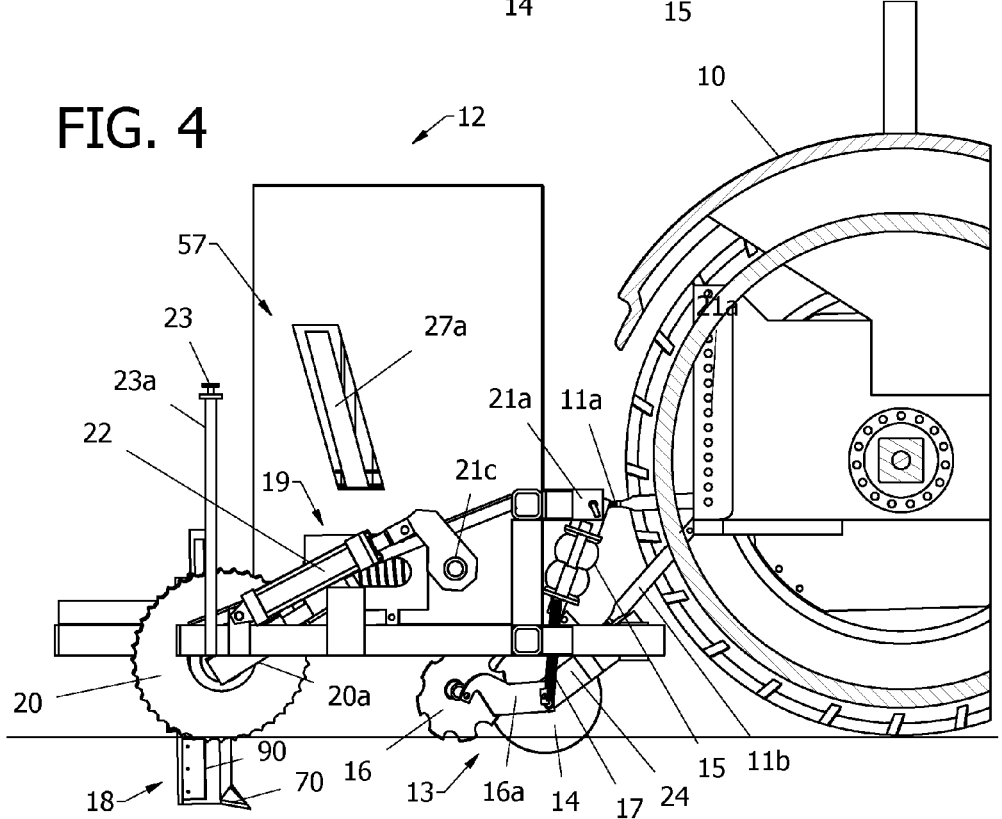

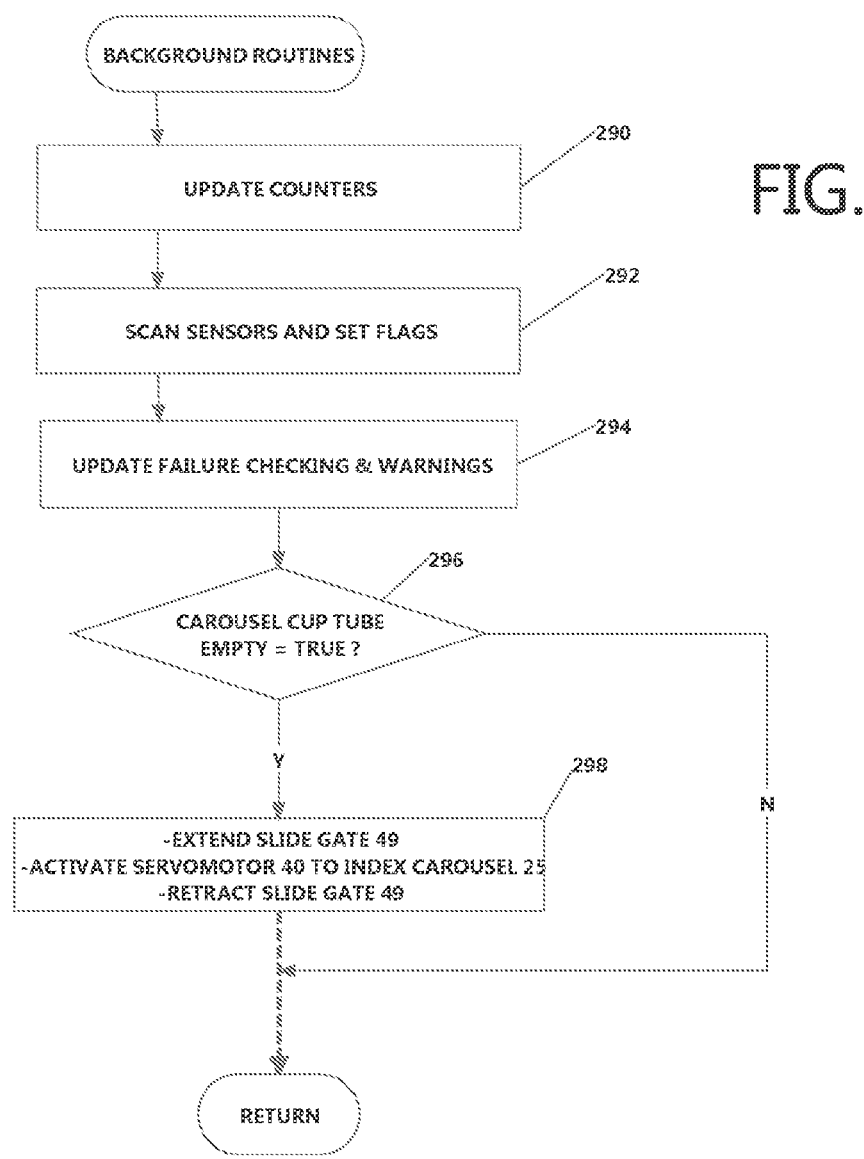

US 9,500,567 B2

SOIL SAMPLER

RELATED APPLICATIONS

This application is a continuation-in-part of U.S. patent application Ser. No. 13/686,014, filed on Nov. 27, 2012, now U.S. Pat. No. 9,116,078.

TECHNICAL FIELD

This disclosure generally relates to soil sample collection and analysis, and more particularly to a soil sampler that automatically acquires and stores soil samples while being drawn through a farm field.

BACKGROUND OF THE INVENTION

Soil samples (usually the top 7 inches or so of the topsoil) are taken from farm fields and sent to a soil analysis lab to analyze the different soil nutrients contained in the samples. This analysis is used to determine the correct amount of nutrients to apply to farm fields. In the past, the process of collecting the soil samples was a slow tedious job done with a hand probe. Recently some automation has been added to soil sampler equipment to remove some of the hard work, but none have significantly increased the speed of sampling.

There is considerable variability of nutrient content in soil samples taken from different locations in a farm field. The only way to accurately measure this variability is to increase the number of samples taken within a field. But with conventional soil sampling techniques and mechanisms, this can become cost prohibitive due to the time required to collect the samples. Accordingly, what is needed is an improved and automated way of consistently and reliably acquiring soil samples for nutrient analysis.

SUMMARY OF THE INVENTION

The present invention is directed to an automated soil sampler that is removably mounted on an agricultural tractor, and that collects soil samples in a farm field while the tractor is driven through the field. The operator of the tractor manages the operation of the soil sampler from the cab of the tractor. At a periodic interval, the soil sampler lowers a soil collection knife into the soil for approximately 5 seconds to collect a soil sample, raises the collection knife out of the soil, and places the collected soil sample into a bar-coded storage container. When the soil sampler lowers the collection knife into the ground, it notes the GPS location of the soil sample and associates the noted GPS location with the storage container's bar-code in a data file. The interval between successive periodic soil samples corresponds to a determined forward displacement of the tractor (such as 150'). Storage containers that have received soil samples are moved to a storage area until all of the soil samples for a given field have been collected.

The soil sampler includes a soil breakdown assembly that leads the soil collection knife in preparation for soil sampling. The soil breakdown assembly includes an in-line rotating disk longitudinally aligned with the soil collection knife for cutting an initial furrow in the soil to be sampled, and an inwardly-toed slotted disk that shoves aside rocks, plant matter and other debris so that relatively clean soil is confronted by the soil collection knife. The collection knife has a series of sampling chambers that collect samples of topsoil at different soil depths, and a canted press wheel laterally offset from the collection knife urges soil into the sampling chambers as the collection knife is drawn through the soil by the forward movement of the tractor.

The soil sampler further includes a carrousel that carries empty storage cups, and a cup mover assembly that receives empty storage cups from the carrousel and places one of them in a soil receiving station. A spout mechanism transfers a soil sample from the sampling chambers of the collection knife to the empty storage cup in the soil receiving station, and the filled storage cup is then transferred to a storage area.

With the disclosed soil sampler, the time required to collect soil samples has been greatly reduced, significantly increasing the number of samples that can be collected per hour. This greatly increases the precision and accuracy of nutrient maps developed from the soil sample lab results without significantly increasing the sample collection cost. And with accurate nutrient maps, farmers need only apply nutrients where needed, reducing environmental risk and improving profitability.

BRIEF DESCRIPTION OF THE DRAWINGS

FIG. 3 is a close up view of soil sampler as depicted in FIG. 1, but sectioned to reveal critical soil sampling components.

FIG. 4 is a close up view of soil sampler as depicted in FIG. 2, but sectioned to reveal critical soil sampling components.

FIGS. 15a, 15b, 15c and 15d depict a flow diagram representative of software code executed by the microcontroller of FIG. 16 for controlling the operation of the disclosed soil sampler.

DETAILED DESCRIPTION

Figure 1:
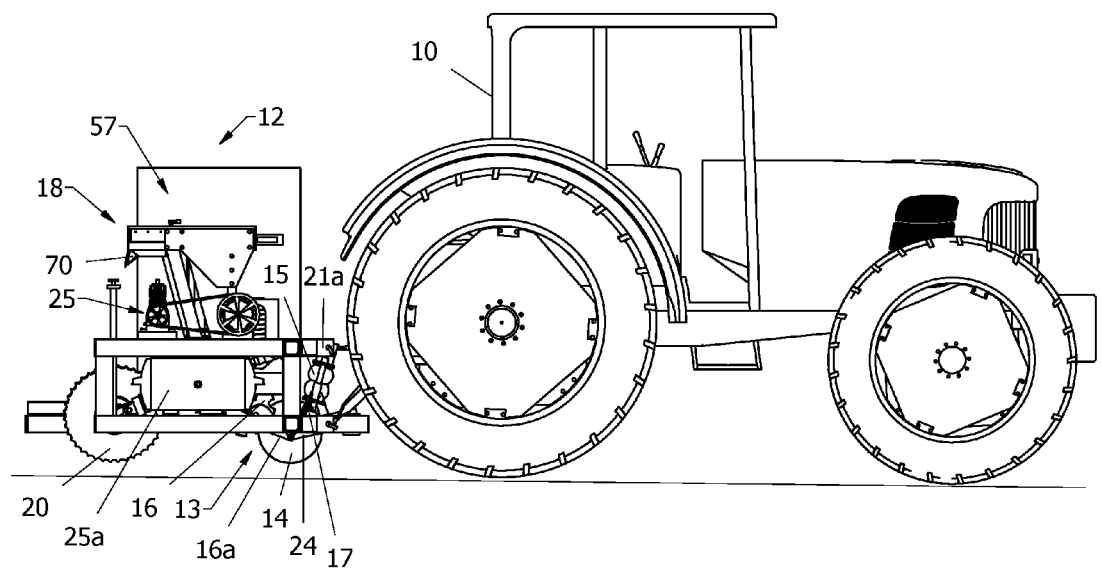
FIG. 1 is a side view of a tractor and an automated soil sampler according to this invention, with the soil sampler in its transport position.
Figure 5:
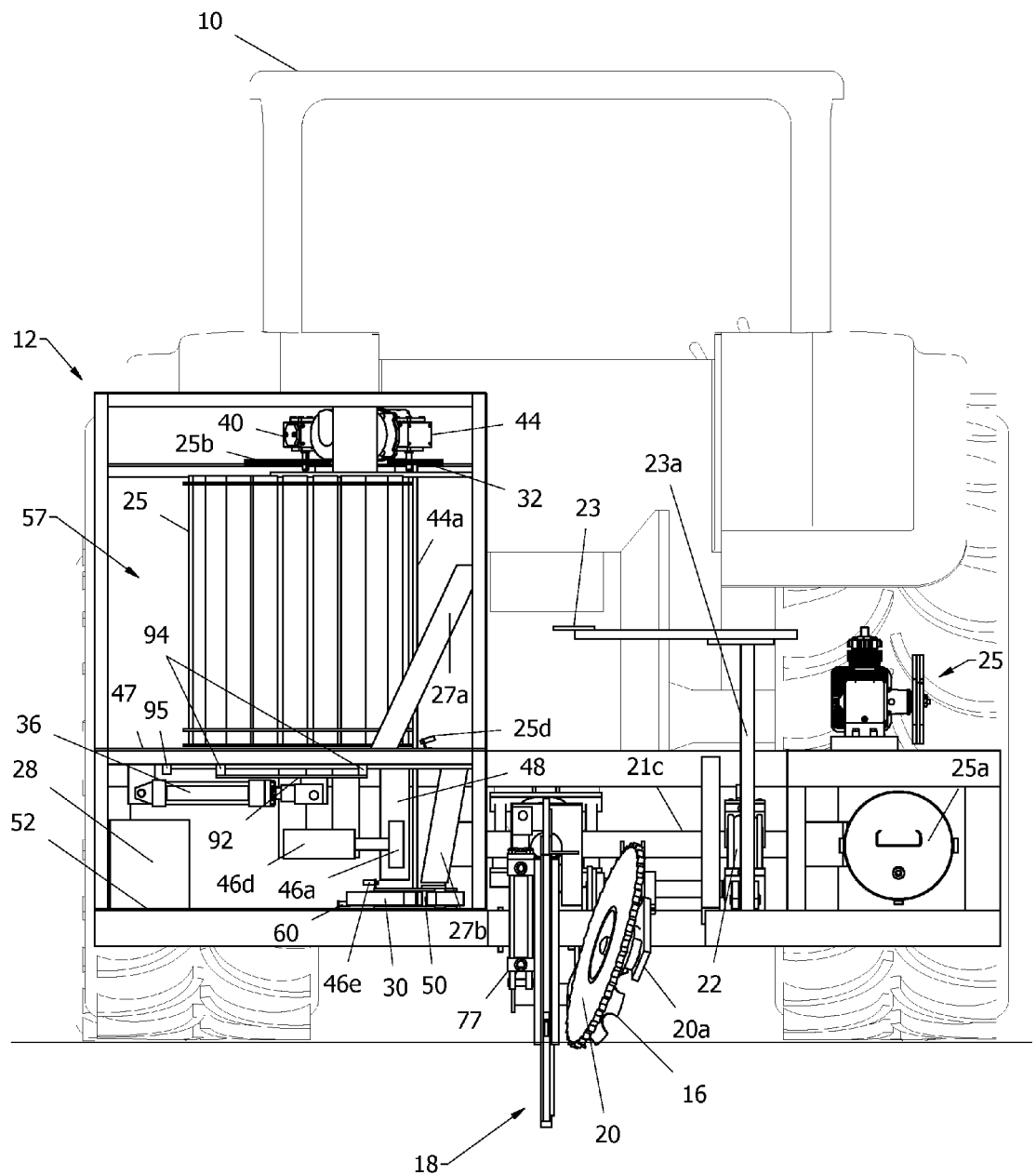
FIG. 5 is a rear view of the soil sampler in its working position, and the soil collection knife lowered.
Figure 6:
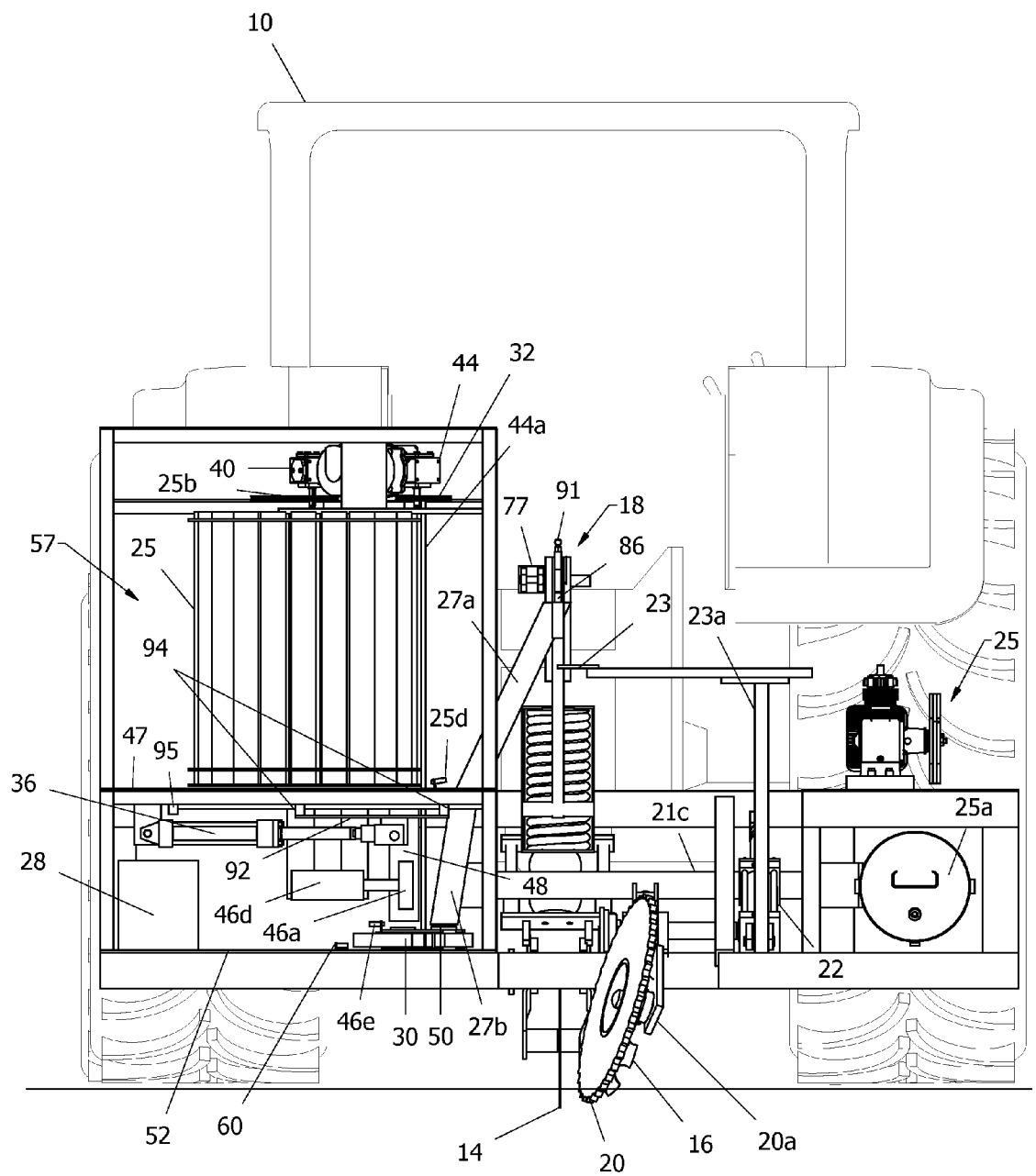
FIG. 6 is a rear view of the soil sampler in its working position, and the soil collection knife raised.
Figure 7:
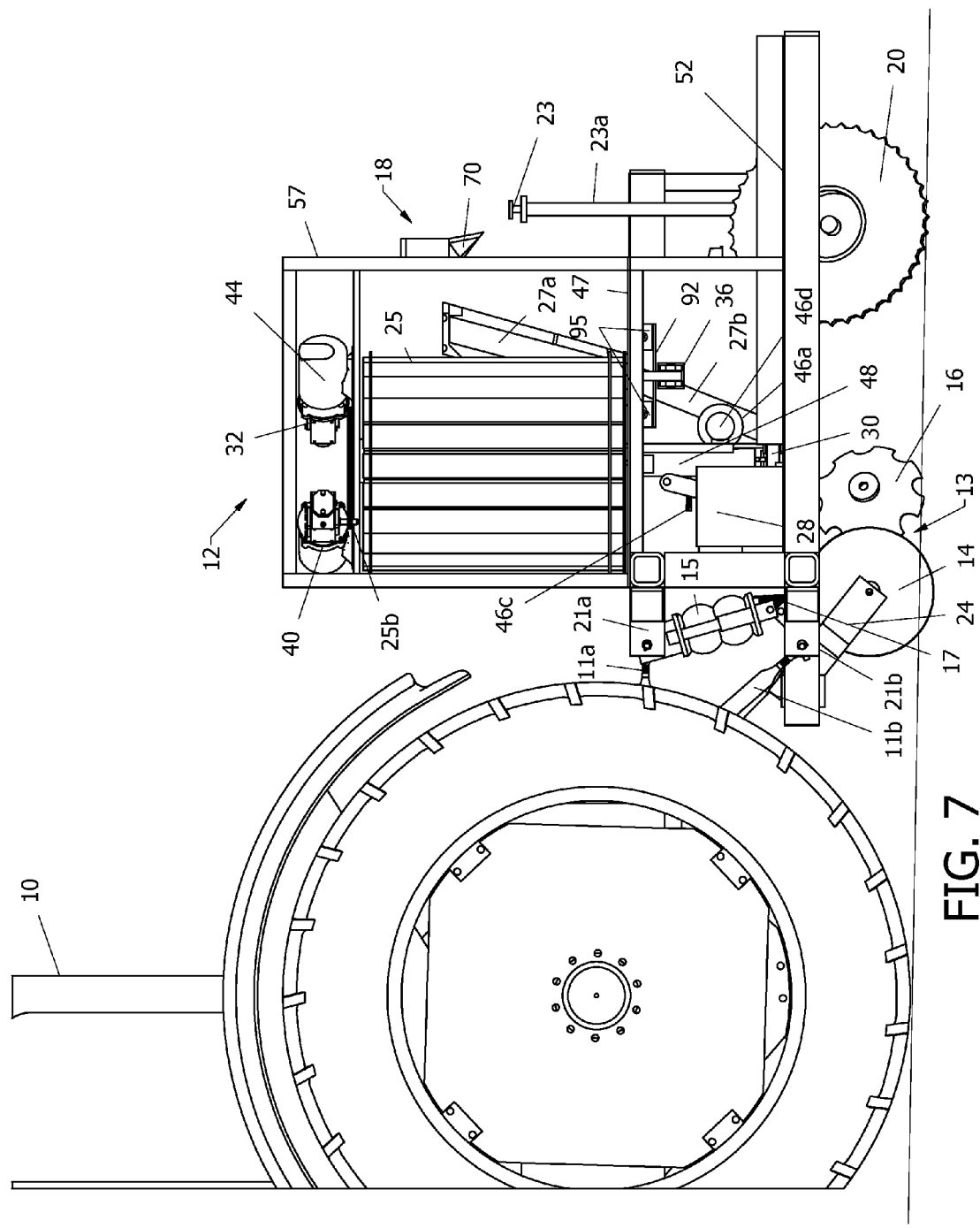
FIG. 7 is an opposite side view of the soil sampler with outer covering removed to reveal the cup carrousel.

FIGS. 1-7 variously depict a soil sampler 12 according to this invention, as mounted on a conventional three-point hitch of a tractor 10. As best seen in FIG. 7, the top link 11a of the three-point hitch is coupled to an upper frame element 21a, and the lift arms 11b of the three-point hitch are coupled to a lower frame element 21b. FIGS. 1 and 3 show the soil sampler 12 in a transport position with the lift arms 11b raised, while FIGS. 2 and 4-7 show the soil sampler 12 in a working position with the lift arms 11b lowered. A hydraulic system including various solenoid valves and hydraulic valves necessary to the below-described operation of soil sampler 12 is generally designated in FIGS. 5-7 by the reference numeral 28.

The soil sampler 12 includes a soil breakdown assembly 13 that prepares the soil for sample collection and a soil collection knife 18 that is momentarily lowered into the soil rearward of the soil breakdown assembly 13 to collect soil at several different soil depths, and then raised to expel the collected soil for transfer to a soil storage mechanism 57. The soil breakdown assembly 13 is located forward of the lowered soil collection knife 18, and includes two rotary members that rotate with forward displacement of the tractor 10 when the soil sampler 12 is in the working position. The rotary members include a leading in-line disk 14, and an inwardly-toed slotted disk 16 following the in-line disk 14. The in-line disk 14 is longitudinally aligned with the soil collection knife 18, and slices open the soil in advance of the soil collection knife 18. The inwardly-toed slotted disk 16 is slightly offset from the initial furrow, and shoves aside rocks, plant matter and other debris so that relatively clean soil is confronted by the soil collection knife 18.

As best seen in FIGS. 3, 4 and 7, the soil breakdown assembly 13 is mounted with respect to the lower frame member 21b on a swinging arm 24 such that in-line disk 14 and inwardly-toed disk 16 are raised above the ground when the soil sampler 12 is in its transport position (FIG. 3) and lowered into contact with the ground when the soil sampler 12 is in its working position (FIGS. 4 and 7). The inwardly-toed disk 16 is supported on an arm 16a that pivots about the axle of in-line disk 14, and a spring 17 biases inwardly-toed slotted disk 16 against the soil. An air bag 15 disposed between upper frame member 21a and the swinging arm 24 is selectively inflated as described below to bias in-line disk 14 into the soil whenever the soil collection knife 18 is lowered.

Figure 11:
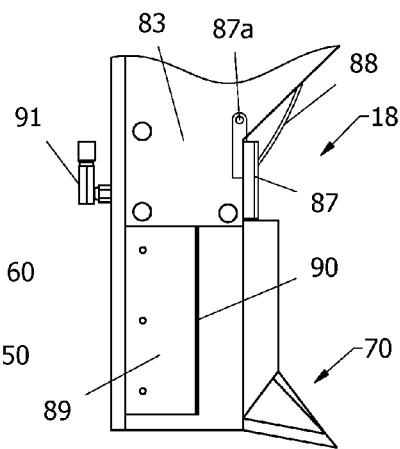
FIG. 11 is a close up view of the soil collection knife.
Figure 13:
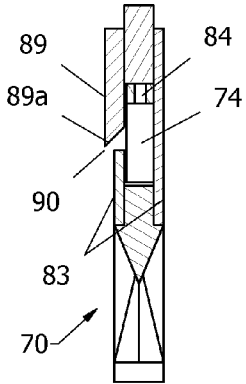
FIG. 13 is a sectional view of the soil collection knife taken along line 13-13 of FIG. 12.
Figure 12:
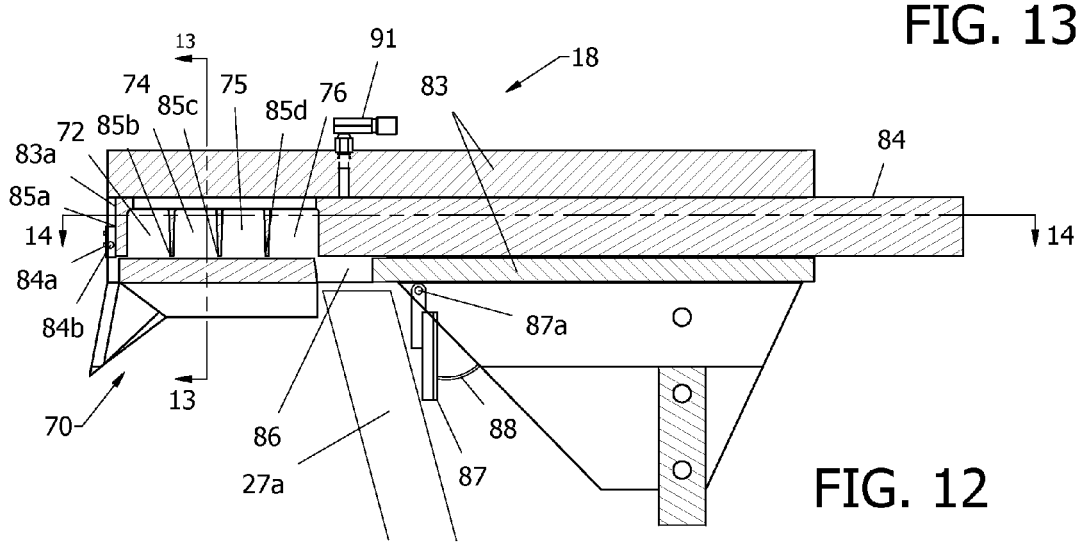
FIG. 12 is a sectional view of the soil collection knife taken along line 12-12 of FIG. 8.
Figure 12A:
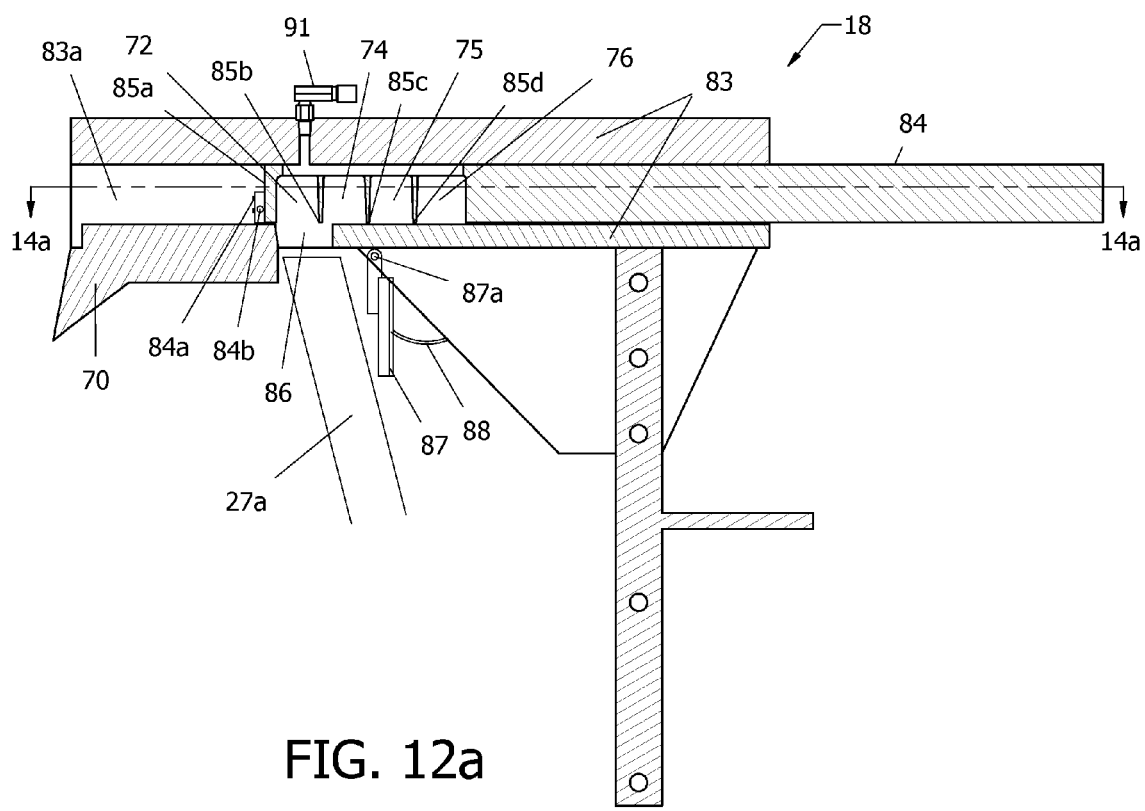
FIG. 12a is a sectional view of the soil collection knife as in FIG. 12, but with the armature retracted to expel a soil sample.

As best seen in FIGS. 11-13, the soil collection knife 18 has a metal housing 83 that terminates in a knife blade 70 which cuts through the soil in the furrow opened by in-line disk 14. A longitudinal cavity 83a spans the length of housing 83, and knife blade 70 is open on one side to expose the cavity 83a, as best seen in FIGS. 12 and 12a. A metal plate 89 fastened to housing 83 partially covers the knife blade opening to form a soil capture slot 90 that spans the height of the knife blade 70, as best seen in FIGS. 11 and 13. The leading edge of the plate 89 is inwardly beveled as shown in FIG. 13 to form a cutting edge 89a that shears off a thin sliver of soil as the soil collection knife blade 70 is drawn through the soil, and directs the sheared-off soil through the soil capture slot 90 and into the cavity 83a. Advantageously, the plate 89 is adjustably fastened to the housing 83 so that the width of the soil capture slot 90 can be increased or decreased to suit the condition of the soil being sampled. As explained below, the housing 83 of soil collection knife 18 additionally includes a soil release opening 86 above the knife blade 70 through which a collected soil sample is expelled once the soil collection knife 18 has been raised.

Figure 2:
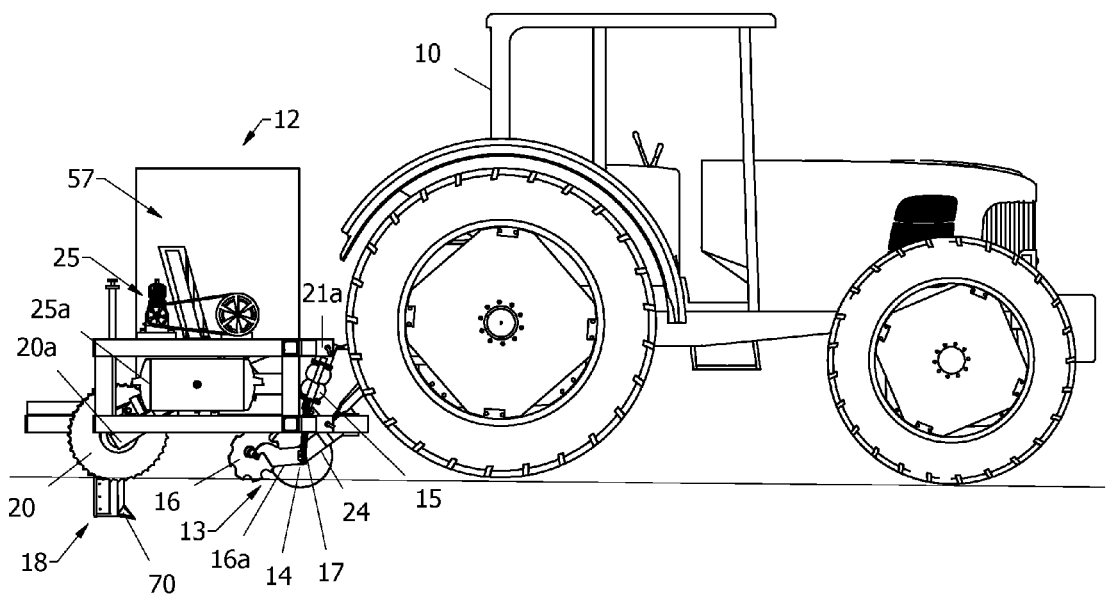
FIG. 2 is a side view of a tractor and an automated soil sampler according to this invention, with the soil sampler in its working position, and the soil collection knife lowered.

As best seen in FIGS. 3-4, the soil collection knife 18 is part of a collection knife assembly 19, and the assembly 19 is mounted on a tubular member 21c that is pivotably supported by the soil sampler frame. A hydraulic cylinder 22 mounted on the soil sampler frame is selectively extended to rotate the collection knife assembly 19 toward tractor 10 and thereby raise the soil collection knife 18, or retracted to rotate the collection knife assembly 19 away from tractor 10 and thereby lower the soil collection knife 18 into the soil to be sampled. FIGS. 2 and 4-5 illustrate the soil collection knife 18 in the lowered position, and FIGS. 1, 3 and 6-7 illustrate the soil collection knife 18 in the raised position. In use, the soil collection knife 18 is only lowered when the soil sampler 12 is in its working position.

As best seen in FIGS. 5-6, a resilient wiper 23 is clamped in a support bracket 23a, and the support bracket 23a is mounted on the soil sampler frame in proximity to the collection knife assembly 19 such that the knife blade 70 brushes against the wiper 23 each time the hydraulic cylinder 22 is extended and retracted to raise and lower the soil collection knife 18. Specifically, the wiper 23 brushes across the soil capture slot 90 of the knife blade 70 to scrub off soil or debris clinging thereto.

As best seen in FIG. 5, the soil sampler 12 additionally includes a toothed canted press wheel 20 that is laterally offset from the soil capture slot 90 of knife blade 70. The press wheel 20 is supported on an arm 20a that is pivotally mounted on the frame of soil sampler 12 such that the press wheel 20 is lifted in the air when the soil sampler 12 is in its transport position (FIGS. 1 and 3), and resting on the soil when the soil sampler 12 in its working position (FIGS. 2 and 4-7). With the soil sampler 12 in its working position, the press wheel 20 rolls along the soil surface, and the peripheral teeth of the press wheel 20 prevent it from skidding when it encounters field debris. Due to its canted orientation, press wheel 20 biases the surface soil laterally towards the soil capture slot 90 of knife blade 70 to ensure consistent and reliable sampling of soil lying near the ground surface.

Figure 14:
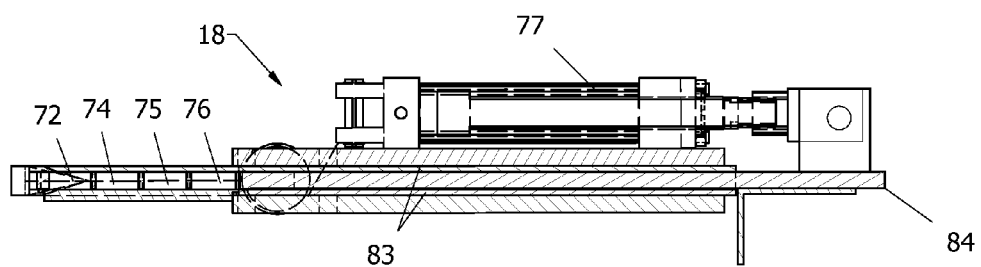
FIG. 14 is a sectional view of the soil collection knife taken along line 14-14 of FIG. 12.
Figure 14A:
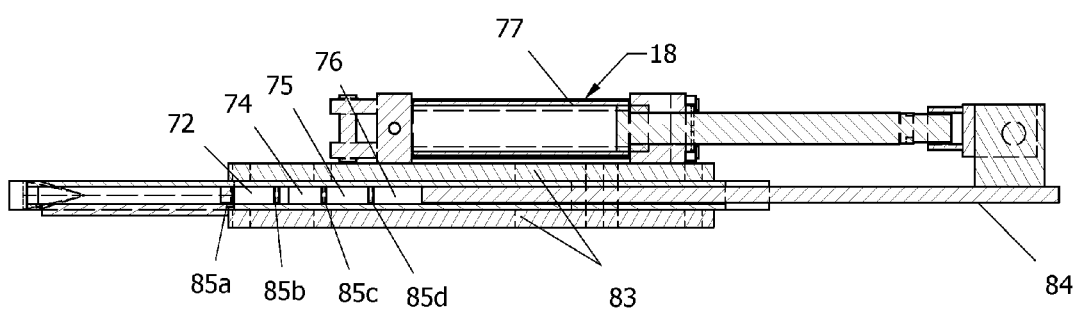
FIG. 14a is a sectional view of the soil collection knife as in FIG. 14, but with the armature retracted to expel a soil sample.

As illustrated in FIGS. 11-14, the knife blade 70 of soil collection knife 18 incorporates a series of four sampling chambers 72, 74, 75, 76 inboard of the soil capture slot 90. The sampling chambers 72, 74, 75, 76 are disposed at different soil depths to collect samples of topsoil at different soil depths, and the canted press wheel 20 urges soil into the sampling chambers 72, 74, 75, 76 as the knife blade 70 is drawn through the soil by the forward movement of the tractor 10. The sampling chambers 72, 74, 75, 76 are physically defined by the housing 83 of soil collection knife 18 and the teeth 85a, 85b, 85c, 85d of a linear armature 84 slidably received within the housing cavity 83a. The teeth 85a -85d are disposed at the outboard end of armature 84, and the position of armature 84 within the housing 83 is controlled by a hydraulic cylinder 77, as best seen in FIG. 5 and 14-14a. FIGS. 12, 14 and 12a, 14a respectively depict extended and retracted positions of the armature 84. When the hydraulic cylinder 77 is retracted as shown in FIGS. 12 and 14, the armature 84 is fully extended into the knife blade 70, and the teeth 85a -85d of armature 84 are aligned with the soil capture slot 90 to collect soil samples. When the hydraulic cylinder 77 is extended as shown in FIGS. 12a and 14a, the armature 84 is retracted from knife blade 70 so that the collected soil samples in sampling chambers 72, 74, 75, 76 can be expelled through the soil release opening 86 of housing 83. A swinging panel or trap door 87 covers the soil release opening 86 when the soil collection knife 18 is lowered (as illustrated in FIG. 11) to prevent soil from entering the soil release opening 86, and uncovers the opening 86 when the soil collection knife 18 is raised (as illustrated in FIGS. 12 and 12a) to allow the collected soil sample to be expelled. As shown in FIGS. 12 and 12a, the trap door 87 pivots about a pin 87a and a cable 88 coupling the trap door 87 to a frame member of soil sampler 12 affirmatively opens the trap door 87 when the soil collection knife 18 is raised.

The armature 84 can be advantageously equipped with a slot clean-out attachment 84a, as best seen in FIGS. 12 and 12a. In the illustrated embodiment, the clean-out attachment 84a is removably fastened the outboard end of armature 84, and includes a tab 84b that protrudes through the soil capture slot 90 just beyond the outermost armature tooth 85a. Each time the armature 84 is extended and retracted, the tab 84b of clean-out attachment 84a correspondingly moves within the soil capture slot 90 to remove any soil, mud or debris lodged in the soil capture slot 90. This action, along with the wiping action of wiper 23, ensures that the soil capture slot 90 will be fully open and unblocked when the soil collection knife 18 is subsequently lowered to collect the next soil sample.

Figure 8:
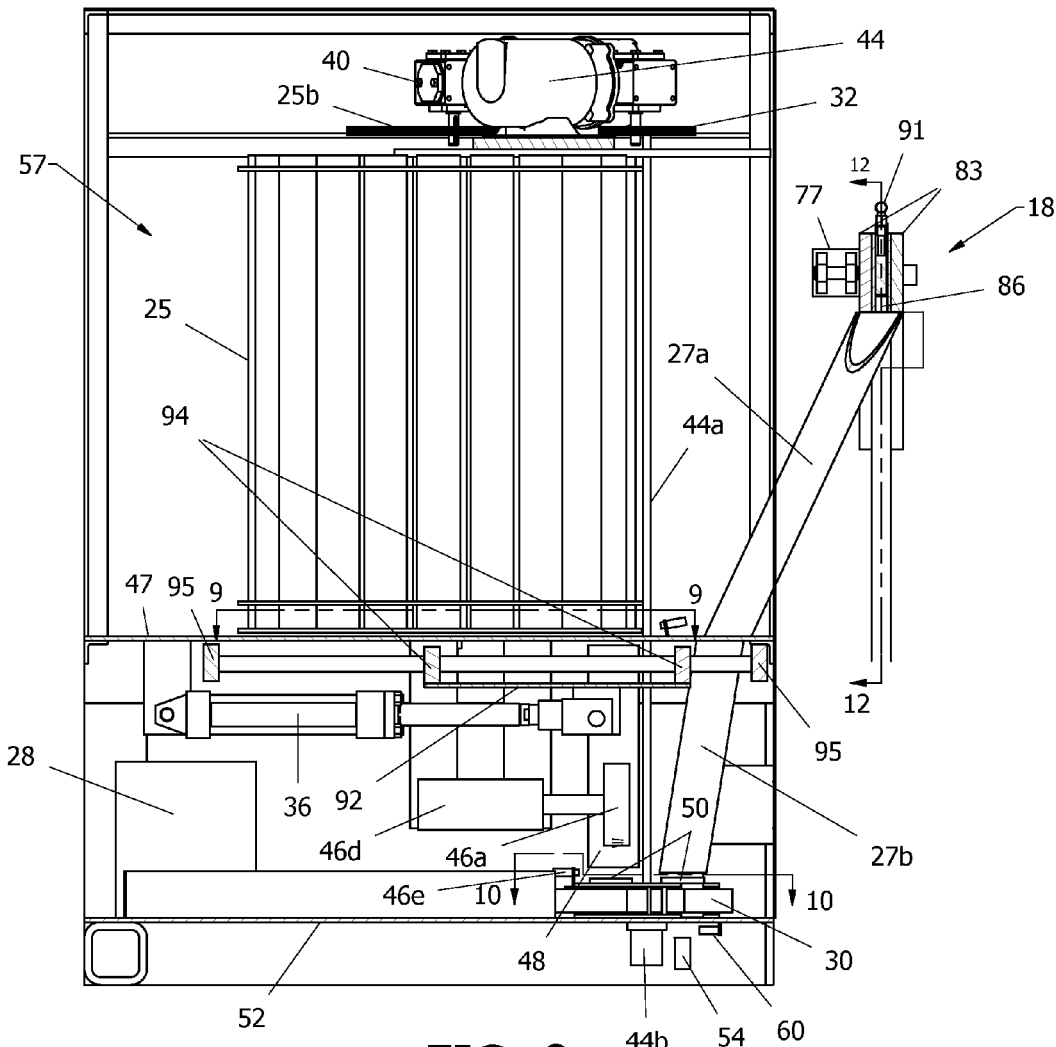
FIG. 8 is a rear view of soil sampler with outer covering removed to reveal the cup carrousel and sample storage apparatus.

After the soil collection knife 18 has been drawn through the soil for a predetermined distance (or time), the hydraulic cylinder 22 is extended to raise the soil collection knife 18 out of the soil as illustrated in FIG. 6. As the soil collection knife 18 is being raised, the trap door 87 swings open to uncover soil release opening 86, and once the soil collection knife 18 is fully raised, a movable spout 27a is positioned under the soil release opening 86, as illustrated in FIGS. 6 and 8. The hydraulic cylinder 77 is then extended to bring the teeth 85a -85d of armature 84 into registry with the soil release opening 86 to expel the soil sample. In practice, the hydraulic cylinder 77 is cycled several times to produce repeated fore and aft movement of the armature 84 within the collection knife housing 83 to dislodge the soil samples from the sampling chambers 72, 74, 75, 76. Additionally, an air nozzle 91 blows high-pressure air into the sampling chambers 72, 74, 75, 76 as they come into registry with the soil release opening 86 to help expel the soil sample, as illustrated in FIG. 12a. Compressed air for this and other purposes mentioned herein is obtained from an on-board air compressor 25 and pressure tank 25a, depicted in FIGS. 1-2.

The soil expelled through the soil release opening 86 drops into the movable spout 27a, which together with a fixed spout 27b, transfers the soil to a storage cup 50 positioned by a cup mover assembly 30 of the soil storage mechanism 57, as seen in FIGS. 6 and 8. Once the soil sample has been dislodged and transferred to the storage cup 50, the movable spout 27a is retracted, allowing the soil collection knife 18 to be lowered to collect the next soil sample.

While all of the sampling chambers 72, 74, 75, 76 can be combined for producing a composite of the soil profile as described above, it is alternatively possible to individually expel and collect the soil collected in sampling chambers 72, 74, 75, 76 if desired. That would provide separate soil samples at various depths in the location where the samples are collected.

As best seen in FIGS. 5-6 and 8, the movable and fixed spouts 27a, 27b cooperate to transfer a collected soil sample from the soil release opening 86 of soil collection knife 18 to a storage cup 50 positioned by cup mover assembly 30. The fixed spout 27b is mounted above the storage cup 50 at an angle defined by the relative locations of the storage cup 50 and the soil release opening 86. Both ends of the fixed spout 27b are open, and the lower end is positioned just above the collection cup 50. The movable spout 27a is mounted on one end of a slide plate 92, at an angle defined by the relative locations of the soil release opening 86 and the upper end of fixed spout 27b. The slide plate 92 is slidably supported in a set of mounting brackets 94, 95 on the underside of a platform 47 above the cup mover assembly 30, and a hydraulic cylinder 36 mounted on the underside of platform 47 is coupled to the plate 92 for controlling the lateral position of plate 92, and hence, movable spout 27a. When the hydraulic cylinder 36 is fully retracted, as shown in FIG. 5, the movable spout 27a is in a home position, allowing the soil collection knife 18 to be lowered and then raised as described above. When the hydraulic cylinder 36 is fully extended, as shown in FIGS. 6 and 8, the movable spout 27a is in a soil transfer position in which its lower end is aligned with the upper end of fixed spout 27b, and its upper end is positioned under the soil release opening 86 of soil collection knife 18. In this soil transfer position, a soil sample expelled from the soil release opening 86 is routed to the collection cup 50 through the combination of movable spout 27a and fixed spout 27b.

Figure 10:
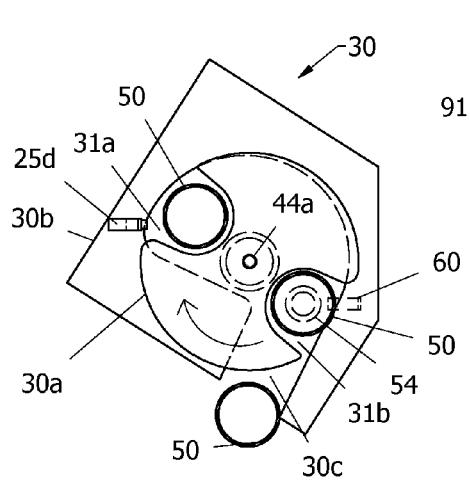
FIG. 10 is a sectional view taken along line 10-10 of FIG. 8 to reveal the cup mover assembly.

As shown in FIG. 8, the cup mover assembly 30 is mounted on a metal platform 52 disposed below the platform 47, and a cup dispensing chute 48 extends downward from the platform 47 toward the cup mover assembly 30 for delivering empty storage cups 50 to the cup mover assembly 30. And as best seen in FIG. 10, the cup mover assembly 30 includes a cup translating member 30a mounted for rotation within a frame 30b. A servomotor 44 is coupled to a central hub of cup translating member 30a via speed reduction gearing 32 and drive shaft 44a for controlling the rotation of cup translating member 30a within the frame 30b, and an encoder 44b senses its rotary orientation. The cup translating member 30a has two oppositely disposed peripheral recesses 31a, 31b, each sized to accommodate a storage cup 50, so that a storage cup 50 placed in a given peripheral recess 31a, 31b rests on the platform 52, and is laterally trapped between the given recess 31a, 31b and the fame 30b.

As best seen in FIG. 8, the cup mover assembly 30 is configured so that when one of the recesses 31a, 31b is vertically aligned with the cup dispensing chute 48 (referred to herein as the cup drop station), the oppositely disposed recess 31b, 31a will be vertically aligned with the lower end of the fixed spout 27b (referred to herein as the soil receiving station). In operation then, the servo motor 44 rotates the cup translating member 30a so that a given peripheral recess 31a, 31b stops in the cup drop station, and after an empty storage cup 50 is dispensed from the chute 48, rotates the cup translating member 30a by 180 degrees so that the empty storage cup 50 is translated to the soil receiving station. At such point, another empty storage cup 50 may be dispensed into the recess 31a, 31b that is in the cup drop station, and a new soil sample from soil collection knife 18 may be routed via the movable and fixed spouts 27a, 27b into the storage cup 50 in the soil receiving station. Thereafter, the servomotor 44 can be activated to rotate the cup translating member 30a by another 180 degrees so that the empty storage cup 50 the in cup drop station is translated to the soil receiving station, and the just-filled storage cup 50 is ejected from the cup mover assembly 30 through an opening 30c in the frame 30b, as illustrated in FIG. 10. The filled storage cups 50 ejected from the cup mover assembly 30 continue to rest on the platform 52 and are pushed rearward of the cup mover assembly 30 onto a storage area portion of the platform 52 where all filled storage cups 50 are temporarily stored. As best seen in FIG. 7, the platform 52 extends well rearward of the cup assembly 30, and in the illustrated embodiment encompasses an area sufficient to hold about 200 storage cups 50.

Figure 15:
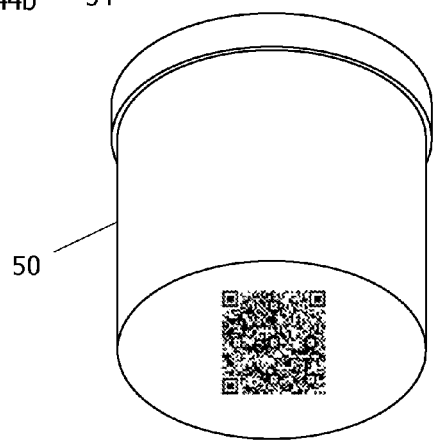
FIG. 15 is an isometric view of a collection cup revealing the bar code on its bottom surface.

As illustrated in FIG. 15, an identification label is affixed to the bottom of each storage cup 50 so that the soil sampler 12 can scan the identification labels as the storage cups 50 are filled with soil samples and store the identification codes along with the corresponding GPS location markers. In the preferred embodiment of this invention, the identification code of a given storage cup 50 is scanned when the storage cup 50 is in the soil receiving station of cup mover assembly 30. To this end, a small opening is formed in platform 52 so that a scanner 54 mounted below the platform 52 can scan the identification code of a storage cup 50 in the soil receiving station of cup mover assembly 30, as best seen in FIG. 8. An air nozzle 60 blows air across the scanner 54 to remove extraneous dirt or other debris that could interfere with the scanning. Other air nozzles may also be directed toward the cup mover assembly 30 to blow away loose dirt that might otherwise interfere with the operation of the moving components.

Figure 9:
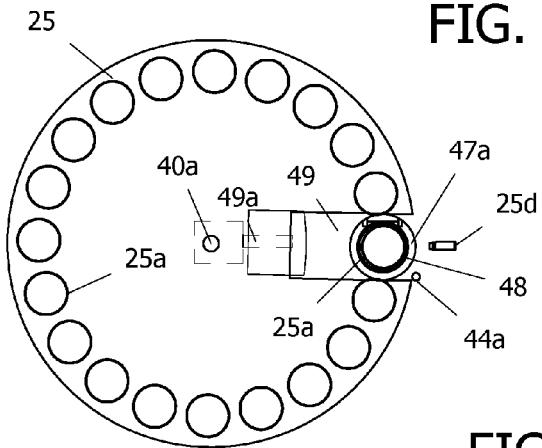
FIG. 9 is a sectional view of the cup carrousel taken along line 9-9 of FIG. 8.

Empty storage cups 50 that will eventually be dispensed into the cup mover assembly 30 as described above are stored in a carousel 25 that is rotatably mounted on the upper surface of platform 47, as best seen in FIG. 8. The empty storage cups 50 are stacked in a number of vertically disposed plastic tubes 25a supported about the periphery of carousel 25, as illustrated in FIGS. 8-9. A servomotor 40 is coupled to carousel 25 via reduction gearing 25b for controllably rotating the carousel 25, and as the carousel 25 is rotated, each of the plastic tubes 25a is successively brought into vertical alignment with the cup dispensing chute 48, as best seen in FIG. 9. The platform 47 has an opening 47a directly above the cup dispensing chute 48, and a slide gate 49 disposed between the carousel 25 and the top of platform 47 can be extended upon activation of an electric motor 49a to cover the opening 47a. In use, the slide gate 49 is extended to cover the opening 47a when the servomotor 40 is activated to rotate the carousel 25, and retracted to uncover the opening 47a once the carousel 25 has been positioned so that one of the plastic tubes 25a is vertically aligned with the cup dispensing chute 48. Once the slide gate 49 has been retracted to uncover the opening 47a (as shown in FIG. 9), the empty soil collection cups 50 stacked in the vertically aligned tube 25a are free to drop into the chute 48. A sensor 25d mounted adjacent the periphery of carousel 25 in vertical alignment with the chute 48 detects when the respective plastic tube 25a is empty of cups 50, signaling that it is time to extend the slide gate 49 and activate servomotor 40 to advance the carousel 25 and bring a different plastic tube 25a into alignment with the chute 48.

Figure 7A:
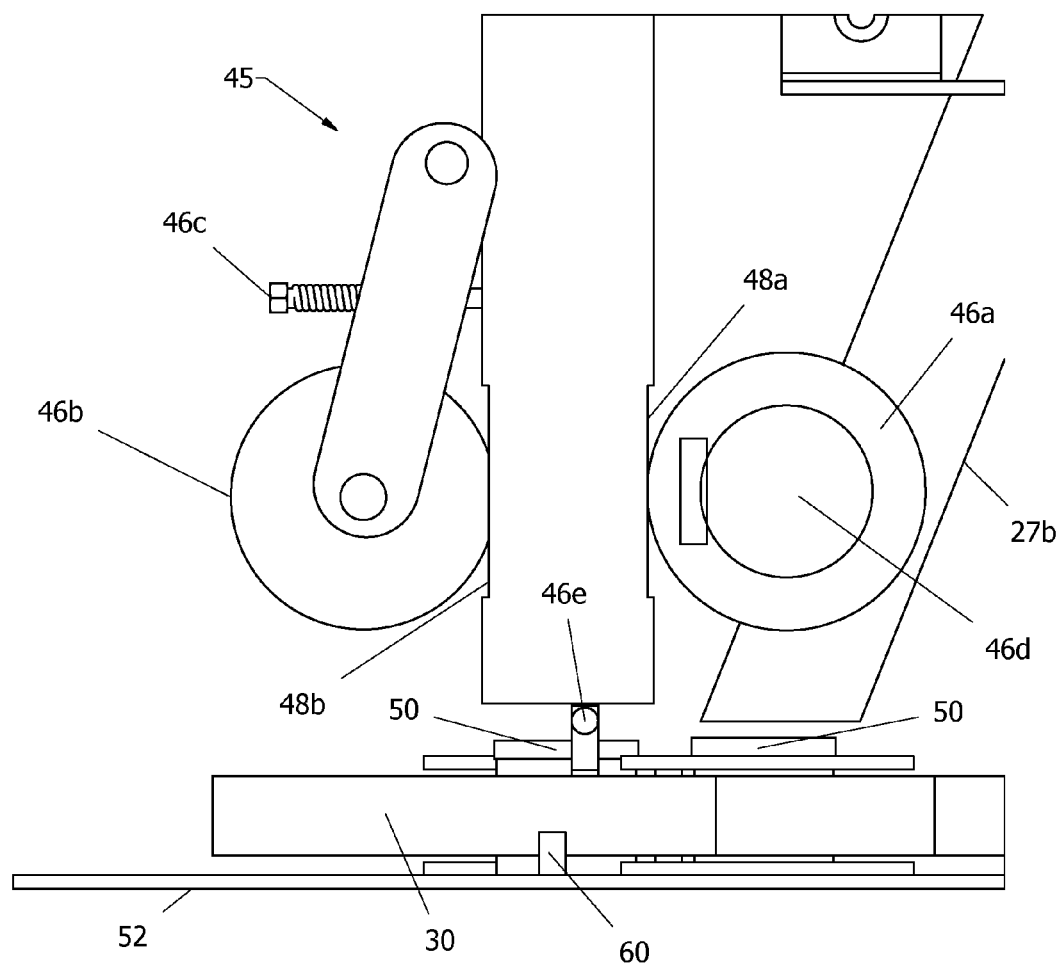
FIG. 7a is a close up view of FIG. 7, sectioned to reveal a cup drop mechanism.

Once a stack of empty storage cups 50 have been dropped into the cup dispensing chute 48, a cup drop mechanism 45 is selectively activated to separate out one storage cup 50 and deliver it to the cup drop station of cup mover assembly 30 as described above. As seen in FIGS. 7, 7a and 8, the cup drop mechanism 45 includes two gripper wheels 46a and 46b oppositely disposed about the chute 48 that slightly protrude into the chute 48 through oppositely disposed openings 48a and 48b formed in the sidewall of chute 48. When a stack of storage cups 50 is dropped into the chute 48, the bottom-most storage cup 50 comes into contact with the periphery of wheels 46a and 46b, and cannot move lower in the chute 48 until the wheels 46a, 46b rotate in a direction to produce downward movement. In the illustrated embodiment, the wheel 46a is a driven wheel, while the wheel 46b is an idler wheel, biased toward the chute by a spring 46c. A servomotor 46d coupled to the axle of wheel 46a is selectively activated to rotate the wheel 46a, and a sensor 46e mounted on platform 52 adjacent cup mover assembly 30 detects the presence or absence of a storage cup 50 in the cup drop station of cup mover assembly 30. In operation, a storage cup 50 is dispensed by activating the servomotor 46d until the sensor 46e detects that a storage cup 50 has been dropped into the cup drop station of cup mover assembly 30, and then deactivating the servomotor 46d.

It should be understood that various limit switches and position encoders are employed to control or confirm completion of the required movements described above, even though such switches and encoders have not been illustrated in order to not overly complicate the drawings.

In order to operate the soil sampler 12, a microprocessor-based controller 112 such as a Renu Model FT4057T-E Controller may be mounted in the cab of tractor 10. The Renu controller, for example, has a number of slots for receiving digital and analog I/O modules, and executes a software program such as generally described by the flow diagram of FIGS. 15a-15d for regulating the operation of soil sampler 12. It will be appreciated that other controllers could alternatively be used. The controller 112 and other electrical system components of the soil sampler 12 are generally depicted in the block diagram of FIG. 16. As indicated, the controller 112 has communication ports for receiving inputs from various devices including the tractor's GPS unit 114, barcode reader 54, motor encoder 44b, and the various other sensors and encoders. Controller 112 also has a USB port for a portable memory device 118 for recordation of the data collected during a soil sampling run, a touch-screen display/interface, and a power supply 120. Power supply 120 has an emergency stop 122, receives power from tractor 10 and outputs both a 12V signal and a 24V signal.

Figure 15A:
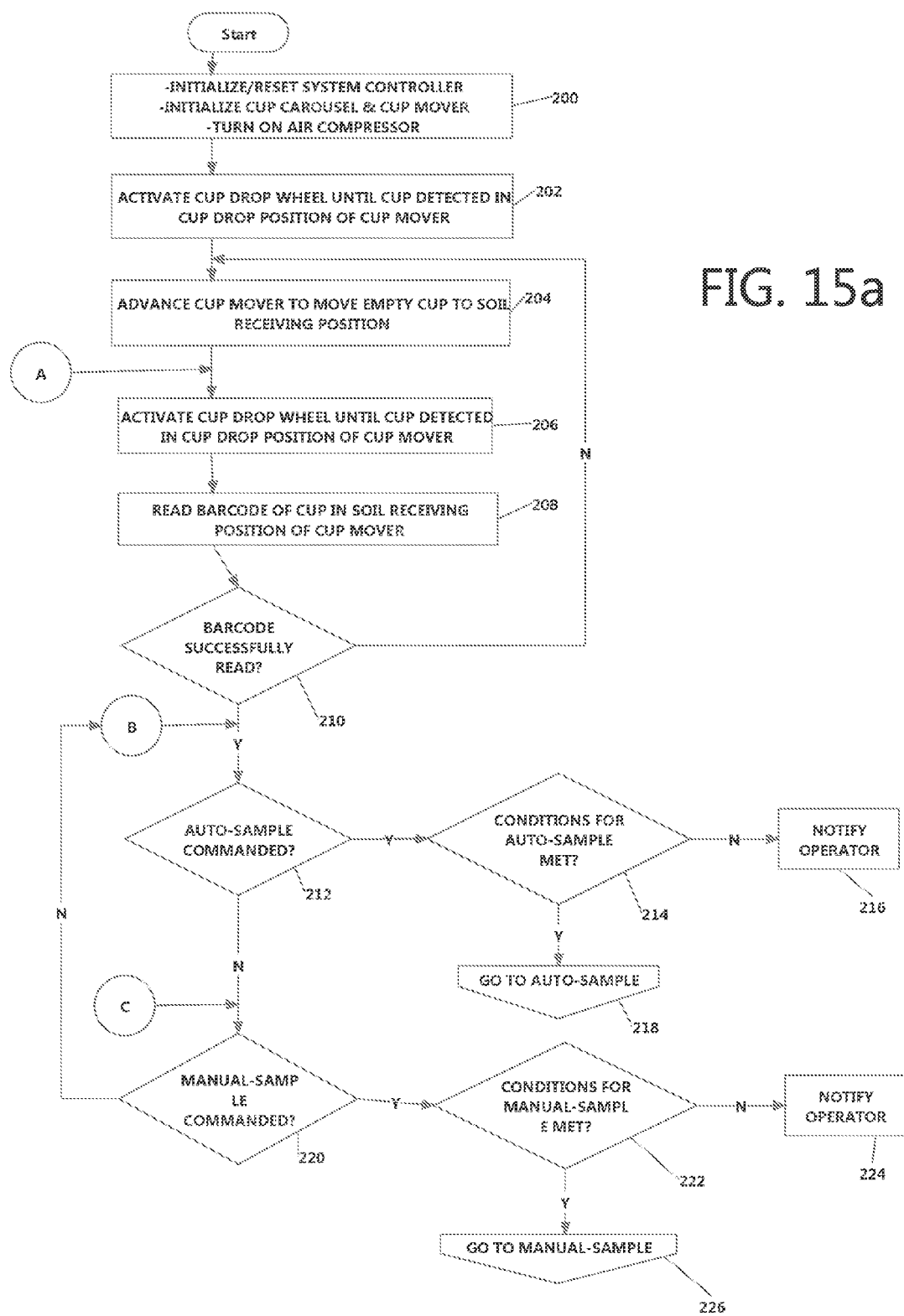
Figure 15B:
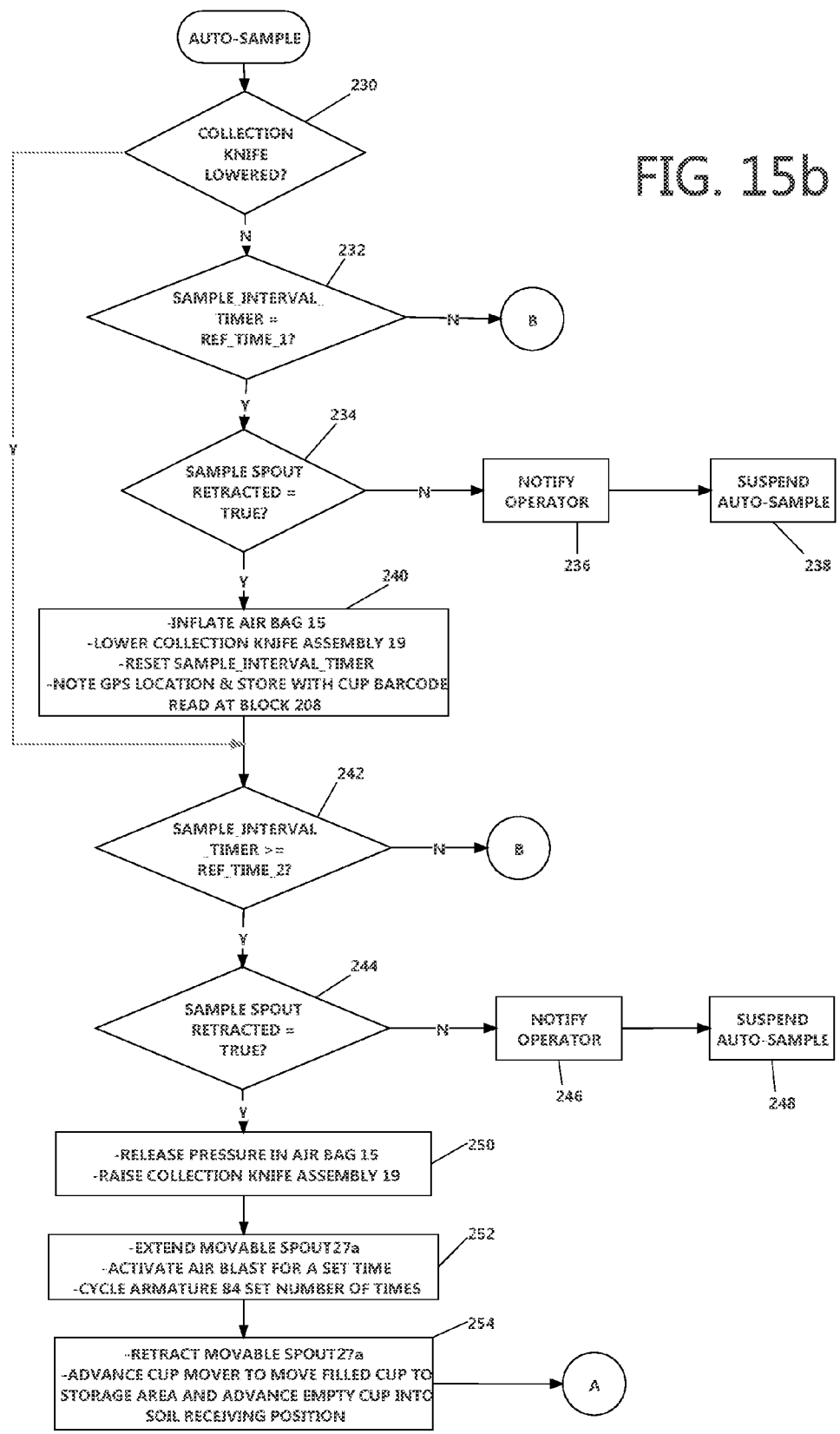
Figure 15C:
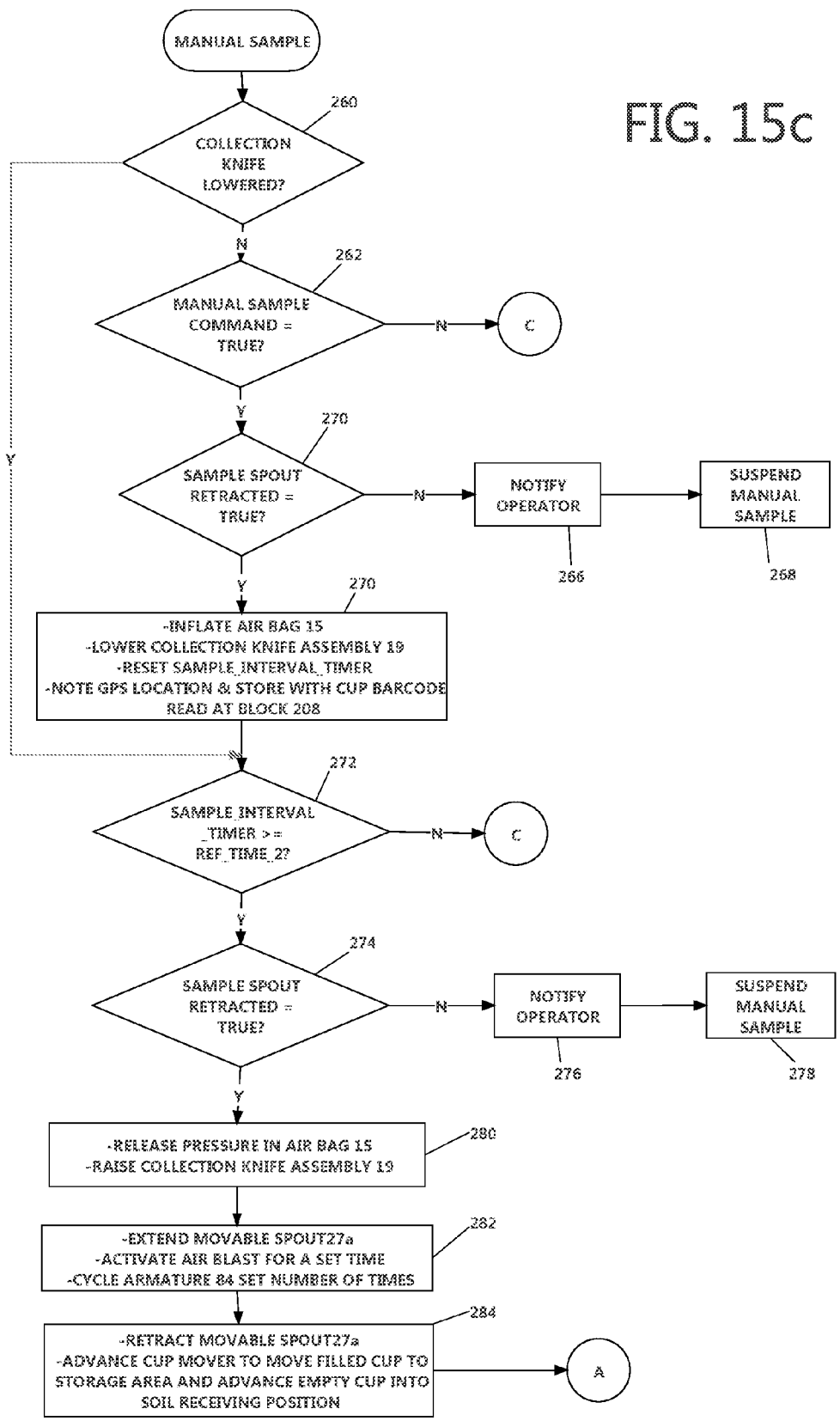
Figure 16:
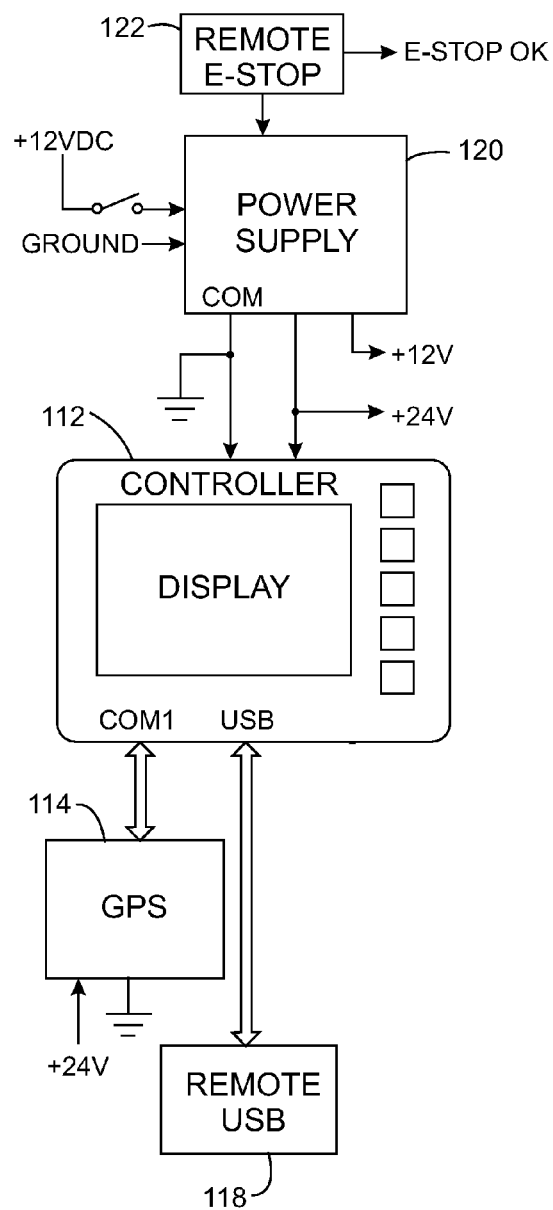
FIG. 16 is a block diagram of a microcontroller of the soil sampler.

FIGS. 15a-15d are flow diagrams representative of software routines executed by the controller 112 of FIG. 16 for controlling the operation of the soil sampler 12. Referring initially to FIG. 15a, soil sampling operation is initialized at block 200 once the operator has moved the tractor 10 into the field to be sampled and lowered the soil sampler 12 into the working position, as depicted in FIG. 2. As indicated at block 200, the initialization process includes initializing/resetting the system controller 112 and the various flags and counters/timers, initializing/homing the carousel 25 and cup mover assembly 30, and turning on an on-board air compressor 25 to build up a supply of compressed air for the various air nozzles.

Following initialization, block 202 is executed to activate the servomotor 46d of cup drop mechanism 45 until an empty storage cup 50 has been dispensed into the cup drop station of cup mover assembly 30, and block 204 is executed to activate servomotor 44 to rotate the cup translating member 30a of cup mover assembly 30 by 180 degrees to move the dispensed storage cup 50 into the soil receiving station. The blocks 206-208 are then executed to re-activate the servomotor 46d until another empty storage cup 50 has been dispensed into the cup drop station, and to activate the scanner 54 to read the identification code of the storage cup 50 resting in the soil receiving station. The air nozzle 60 is also activated at this time to clear the scanner 54 of any soil or debris. If the identification code is not successfully read, as determined at block 210, it is assumed either that there is no storage cup in the soil receiving station, or that the cup's identification code has been damaged or obscured for some reason; in this case, the blocks 204-208 are re-executed to advance the cup translating member 30a of cup mover 30 by 180 degrees, to dispense another empty storage cup 50 into the cup drop station, and to scan the identification code of the storage cup 50 now resting in the soil receiving station.

When block 210 confirms that the identification code of the storage cup 50 in the soil receiving station has been successfully scanned, the remaining blocks 212-226 of FIG. 15a are executed as indicated to determine the sampling mode (i.e., automatic or manual), and if the soil sampler 12 is ready to initiate sampling. If the operator has requested initiation of automatic sampling (AUTO-SAMPLE), block 212 is answered in the affirmative, and block 214 determines if the conditions for the auto-sample mode have been met. These conditions may include, for example, soil sampler 12 in working position, tractor 10 moving forward at the specified speed, movable spout 27a retracted, etc. If one or more of the conditions are not met, block 216 is executed to notify the operator so that the required change(s) can be made—for example, the display of controller 112 may be used to advise the operator to lower the soil sampler 12 to the working position. Once the conditions have been met, block 218 directs the controller 112 to execute the auto-sample routine, which is represented by the flow diagram of FIG. 15b.

In a similar way, block 220 determines if the operator has requested initiation of manual sampling (MANUAL-SAMPLE). The manual sampling mode differs from automatic sampling in that the operator manually initiates the collection of each soil sample as the tractor 10 is driven though the field. If block 220 is answered in the affirmative, block 222 determines if the conditions for the manual-sample mode have been met. These conditions may be the same or similar to the conditions for automatic sampling mentioned above in reference to block 214. If one or more of the conditions are not met, block 224 is executed to notify the operator so that the required change(s) can be made; and once the conditions have been met, block 226 directs the controller 112 to execute the manual-sample routine, which is represented by the flow diagram of FIG. 15c.

Referring now to the auto-sample routine of FIG. 15b, the block 230 is first executed to determine if the soil collection knife 18 is already lowered. Initially of course, block 230 will be answered in the negative, and blocks 232-240 are executed to initiate sample collection at the proper time. A timer value (Sample_Interval_Timer) measures the time since the last soil sample was initiated; it is compared to a first reference time (Ref_Time_1) at block 232 to determine when it is time to initiate soil sample collection, and to a second reference time (Ref_Time_2) at block 242 to determine when it is time to raise the soil collection knife 18 and expel the collected soil sample.

As mentioned above, block 230 will initially be answered in the negative, and block 232 is executed to compare Sample_Interval_Timer to Ref_Time_1. The timer Sample_Interval_Timer is initialized to zero at system initialization, and block 232 will be answered in the negative until it reaches Ref_Time_1, which may correspond to a calibrated time interval such as 45 seconds, where 45 seconds at 5 MPH yields a distance of 330 feet between samples. When block 232 is answered in the negative, the controller 112 is directed back to block 212 of FIG. 15a, as indicated by the circled letter B. When Sample_Interval_Timer reaches Ref_Time_1, it is time to collect a soil sample, but block 234 is executed first to make sure the movable spout 27a is retracted; if not, the blocks 236 and 238 are executed to notify the operator and to suspend sampling until the spout 27a is retracted. If the spout 27a is retracted, block 240 is executed to pressurize air bag 15 for producing additional down force on the in-line disk 14, to lower the soil collection knife 18, to reset Sample_Interval_Timer, and to note the GPS latitude and longitude readings and tag them to the storage cup identification code scanned at block 208. In subsequent executions of the routine, block 230 will be answered in the affirmative so that the controller 112 will skip blocks 232-240 as indicated.

Once the soil collection knife 18 has been lowered to initiate soil sampling, the controller 112 periodically executes block 242 to determine if it is time to raise the soil collection knife 18 and expel the soil sample. As indicated above, block 242 compares Sample_Interval_Timer to Ref_Time_2, which may correspond to a calibrated time interval such as 7 seconds. Initially, of course, block 242 will be answered in the negative, and the controller 112 is directed back to block 212 of FIG. 15a, as indicated by the circled letter B. When Sample_Interval_Timer reaches Ref_Time_2, it is time to raise soil collection knife 18, but block 244 is executed first to make sure the movable spout 27a is retracted; if not, the blocks 246 and 248 are executed to notify the operator and to suspend sampling until the spout 27a is retracted. If the spout 27a is refracted, block 250 is executed to relieve the pressure in air bag 15, and to raise soil collection knife 18. Then block 252 is executed to extend the movable spout 27a, to temporarily activate the air nozzle 91, and to cycle the armature 84 a preset number of times (two, for example) to expel the collected soil through the soil release opening 86 and into the movable spout 27a positioned thereunder. Finally, block 254 is executed retract the movable spout 27a and to rotate the cup translating member 30a of cup mover assembly 30 by 180 degrees so that the storage cup 50 holding the new soil sample is transferred to the cup storage area of platform 52, and the empty storage cup 50 dispensed at block 206 is rotated into the soil receiving station. The controller 112 is then directed back to block 206 of FIG. 15a, as indicated by the circled letter A, where another empty storage cup 50 is dispensed into the cup mover assembly 30, as described above.

Referring to FIG. 15c, the flow chart for the manual sampling mode is similar to the above-described auto-sample flow chart, with one notable exception: the soil collection knife 18 is only lowered to collect a soil sample when the operator activates a Manual Sample Command via controller 112. In the flow chart, the Manual Sample Command is designated as a flag that changes from False to True when the operator activates a manual sample command. To begin the routine, the block 260 is executed to determine if the soil collection knife 18 is lowered. Initially, of course, block 260 will be answered in the negative, and block 262 is executed to determine if the Manual Sample Command is True. If not, the controller 112 is returned to block 220 of FIG. 15a, as indicated by the circled letter C. If block 262 is answered in the affirmative, block 264 is executed to make sure the movable spout 27a is retracted; if not, the blocks 266 and 268 are executed to notify the operator and to suspend sampling until the spout 27a is retracted. If the spout 27a is retracted, block 270 is executed to pressurize air bag 15 for producing additional down force on the in-line disk 14, to lower the soil collection knife 18, to reset Sample_Interval_Timer, and to note the GPS latitude and longitude readings and tag them to the storage cup identification code scanned at block 208. In subsequent executions of the routine, block 260 will be answered in the affirmative so that the controller 112 will skip blocks 262-270 as indicated.

Once the soil collection knife 18 has been lowered to initiate soil sampling, the controller 112 periodically executes block 272 to determine if it is time to raise the soil collection knife 18 and expel the soil sample. As in the auto-sample mode, block 272 compares Sample_Interval_Timer to Ref_Time_2, which may correspond to a calibrated time interval such as 7 seconds. Initially, of course, block 272 will be answered in the negative, and the controller 112 is directed back to block 220 of FIG. 15*a*, as indicated by the circled letter C. When Sample_Interval_Timer reaches Ref_Time_2, it is time to raise soil collection knife 18, but block 274 is executed first to make sure the movable spout 27*a* is retracted; if not, the blocks 276 and 278 are executed to notify the operator and to suspend sampling until the spout 27*a* is retracted. If the spout 27*a* is refracted, block 280 is executed to relieve the pressure in air bag 15, and to raise soil collection knife 18. Then block 282 is executed to extend the movable spout 27*a*, to temporarily activate the air nozzle 91, and to cycle the armature 84 a preset number of times (two, for example) to expel the collected soil through the soil release opening 86 and into the movable spout 27*a* positioned thereunder. Finally, block 284 is executed retract the movable spout 27*a* and to rotate the cup translating member 30*a* of cup mover assembly 30 by 180 degrees so that the storage cup 50 holding the new soil sample is transferred to the cup storage area of platform 52, and the empty storage cup 50 dispensed at block 206 is rotated into the soil receiving station. The controller 112 is then directed back to block 206 of FIG. 15*a*, as indicated by the circled letter A, where another empty storage cup 50 is dispensed into the cup mover 30 assembly, as described above.

Finally, the flow chart of FIG. 15*d* represents a number of background routines periodically executed by the controller 112. These include, for example, updating various counters (block 290), scanning sensors and setting flags accordingly (block 292) and updating failure checking and operator warnings (block 294). More pertinent to the present invention, the blocks 296-298 designate a background routine for controlling rotation of carousel 25. The block 296 checks the status of a flag representing the state of the chute sensor 25*d*; the flag (Carousel_Cup_Tube_Empty) is False when one or more empty storage cups 50 remain in the active cup tube 25*a* (i.e., the cup tube vertically aligned with the cup dispensing chute 48), and True when no empty storage cups 50 remain in the active cup tube 25*a*. Thus, whenever block 296 is answered in the affirmative, block 298 is executed to extend the slide gate 49 to cover the opening 47*a* between carousel 25 and chute 48, to activate the servomotor 40 to rotate the carousel 25 until a full plastic tube 25*a* is vertically aligned with the chute 48, and then to retract the slide gate 49 to uncover the opening 47*a* so that the empty storage cups 50 stacked in the new cup tube 25*a* drop into the chute 48.

In the manner described above, the soil sampler 12 of this invention efficiently carries out automatic or manually-triggered soil sampling and collection while the soil sampler 12 is being drawn through a field by the tractor 10. The samples are collected and stored while the tractor 10 is on the move, and the sample locations are automatically and accurately logged and associated with the respective storage cups 50. Moreover, each soil sample accurately represents a composite of the soil profile at the sampling location, enabling an accurate assessment of the soil nutrient levels. In a typical application, with the soil of a given field being sampled on a one-half acre grid, up to 500 acres (i.e., 1,000 samples) can be sampled in a single day.

While the soil sampler 12 and its operation have been described with reference to the illustrated embodiment, those skilled in the art will understand that various changes may be made and equivalents may be substituted for elements thereof without departing from the scope and essence of the disclosure. In addition, many modifications may be made to the teachings of the disclosure in order to adapt to a particular situation without departing from the essential scope thereof. Therefore, it is intended that the disclosure not be limited to the particular embodiments disclosed, but that the disclosure will include all embodiments falling within the scope of the appended claims.

We claim:

1. A soil sampler adapted to be mounted on a tractor for periodically collecting and storing samples of topsoil from a farm field while the tractor is drawing the soil sampler through the field, the soil sampler comprising:
   a knife assembly that is selectively lowered to collect a sample of topsoil and then raised to expel and collect the sample of topsoil, the knife assembly including a housing that terminates in a knife blade that is driven into the topsoil when the knife assembly is lowered, a linear armature slidably received within the housing and extended into said knife blade when said knife assembly is lowered so as to define a sampling chamber within said knife blade, a soil capture slot in one side of said knife blade for directing a profile of topsoil into said sampling chamber as the knife blade is drawn through the topsoil by movement of the tractor, and a soil release opening in the housing above the knife blade through which the sampled topsoil is expelled when the knife assembly is raised and the armature retracted from said knife blade;
   a sample storage apparatus for storing collected topsoil samples in storage cups; and
   a movable soil transfer spout for transferring topsoil samples expelled from the soil release opening of said knife assembly to said sample storage apparatus.

2. The soil sampler of claim 1, where the knife assembly further comprises:
   a slot clean-out apparatus fastened to an outboard end of the armature, including a tab that protrudes through the soil capture slot of the knife blade and moves within the soil capture slot as the armature is extended and retracted, thereby removing any soil or debris lodged in the soil capture slot.

3. The soil sampler of claim 1, further comprising:
   a resilient wiper positioned by a support bracket in proximity to said knife assembly such that said wiper bushes across the soil capture slot of the knife blade each time the knife assembly is lowered and raised so as to scrub off soil or debris clinging thereto.

4. The soil sampler of claim 1, further comprising:
   a swinging panel that covers said soil release opening when the knife assembly is lowered to prevent soil from entering the soil release opening, and uncovers said soil release opening when the knife assembly is raised to allow the sampled topsoil to be expelled.

5. The soil sampler of claim 4, further comprising:
   a cable coupling said swinging panel to a frame member of said soil sampler so as to ensure that said swinging panel uncovers said soil release opening when the knife assembly is raised.

6. The soil sampler of claim 1, further comprising:
a soil breakdown assembly that, when in a working position, engages the topsoil forward of said knife blade to prepare the topsoil for sample collection, including an in-line disk longitudinally aligned with said knife blade that rotates with forward displacement of the tractor to slice open the topsoil in advance of the knife blade.

7. The soil sampler of claim 6, where said soil breakdown assembly further comprises:
an air bag disposed between said in-line disk and a frame of said soil sampler that is inflated to urge said in-line disk into said topsoil when said knife assembly is lowered.

8. The soil sampler of claim 6, where said soil breakdown assembly further comprises:
an inwardly-toed slotted disk that rotates with forward displacement of the tractor to shove aside rocks, plant matter and other debris so that relatively clean topsoil is confronted by the knife blade.

9. The soil sampler of claim 8, where said soil breakdown assembly further comprises:
a spring element coupled between said inwardly-toed slotted disk and a frame member of said soil sampler to bias said inwardly-toed slotted disk into engagement with said soil.

10. The soil sampler of claim 1, where said sample storage apparatus comprises:
a carousel for storing empty storage cups; and
a cup mover assembly having a cup drop station for receiving an empty storage cup from said carousel, a soil receiving station, and a cup translating member for translating the received empty storage cup to the soil receiving station, the soil receiving station being disposed below a fixed soil transfer spout that cooperates with the movable soil transfer spout to transfer a topsoil sample expelled from the soil release opening of said knife assembly to the empty storage cup in the soil receiving station.

11. The soil sampler of claim 10, where the movable soil transfer spout has upper and lower ends, and is alternately moved between a soil transfer position in which said upper end is positioned under said soil release opening when said is knife assembly is raised and said lower end is aligned with an upper end of said fixed soil transfer spout, and a home position in which the upper end of said movable soil transfer spout is retracted from under said soil release opening to allow lowering of said knife assembly.

12. The soil sampler of claim 10, where said sample storage apparatus further comprises:
a cup dispensing apparatus disposed between said carousel and said cup mover assembly for dispensing an empty storage cup from said carousel to the cup receiving station of said cup mover assembly.

13. The soil sampler of claim 12, where:
said cup dispensing apparatus includes a cup dispensing chute vertically aligned with the cup drop station of said cup mover assembly; and
said carousel includes a set of tubes, each adapted to hold a column of empty storage cups, said carousel being rotatable to successively bring said tubes into vertical alignment with said cup dispensing chute, and a slide gate mechanism selectively activated to cover an opening between said cup dispensing chute and a vertically aligned tube of said carousel to prevent empty storage cups in such tube from dropping into said cup dispensing chute.

14. The soil sampler of claim 13, further comprising:
a sensor for detecting when the empty storage cups held in a tube vertically aligned with said cup dispensing chute have all dropped into said cup dispensing chute; and
a motor drive mechanism responsive to said sensor for activating said slide gate, rotating said carousel to bring a different tube into vertical alignment with said cup dispensing chute, and then deactivating said slide gate to allow empty storage cups held in such different tube to drop into said cup dispensing chute.

15. The soil sampler of claim 12, where:
said cup dispensing apparatus includes a cup dispensing chute vertically aligned with the cup drop station of said cup mover assembly;
said carousel drops a column of empty storage cups into said cup dispensing chute; and
said cup dispensing apparatus includes a cup drop mechanism selectively activated to separate out one of the empty storage cups in said cup dispensing chute for delivery to the cup drop station of said cup mover assembly.

16. The soil sampler of claim 15, where said cup drop mechanism comprises:
a gripper wheel disposed adjacent said cup dispensing chute and protruding though a first opening formed in a sidewall of said cup dispensing chute to engage empty storage cups disposed therein;
a servomotor coupled to rotatably drive said gripper wheel in a direction to produce downward movement of the storage cups in said cup dispensing chute;
a sensor mounted in proximity to the cup drop station of said cup mover assembly for detecting the presence of a storage cup; and
a controller that dispenses a storage cup from said cup dispensing chute to said cup drop station by activating said servomotor until said sensor detects a storage cup.

17. The soil sampler of claim 16, where cup drop mechanism further comprises:
an idler wheel disposed oppositely about said cup dispensing chute from said gripper wheel, and protruding through a second opening formed in a sidewall of said cup dispensing chute opposite said first opening to engage empty storage cups disposed therein.

* * * * *